United States Patent [19]

Untch et al.

[11] 4,145,443
[45] Mar. 20, 1979

[54] BICYCLO[3.1.0]HEXYLETHYLAMINOCARBONYL-SUBSTITUTED NAPHTHYLOXY CARDIOVASCULAR AGENTS

[75] Inventors: Karl G. Untch, Los Altos; Stefan H. Unger, Palo Alto, both of Calif.

[73] Assignee: Syntex (U.S.A.) Inc., Palo Alto, Calif.

[21] Appl. No.: 846,952

[22] Filed: Oct. 31, 1977

[51] Int. Cl.$^2$ .................. C07C 103/29; A01K 31/165
[52] U.S. Cl. .............................. 424/324; 260/307 FA; 260/348.16; 260/465 E; 260/348.46; 560/139; 260/558 R; 260/559 A; 424/272
[58] Field of Search ........... 260/559 A, 558 R, 518 R; 424/324

[56] References Cited

U.S. PATENT DOCUMENTS

| | | | |
|---|---|---|---|
| 3,676,493 | 7/1972 | Smith | 260/559 A |
| 3,723,524 | 3/1973 | Augstein et al. | 260/559 A X |
| 4,000,192 | 12/1976 | Lunts et al. | 260/559 A X |
| 4,000,193 | 12/1976 | Lunts et al. | 260/559 A X |
| 4,059,621 | 11/1977 | Vincent et al. | 260/559 A X |

FOREIGN PATENT DOCUMENTS 1245357  7/1967  Fed. Rep. of Germany ...... 260/559 A

*Primary Examiner*—Allen B. Curtis
*Attorney, Agent, or Firm*—Richard J. Hammond; Gerard A. Blaufarb

[57] ABSTRACT

1-Alkylamino-3-([2-(endobicyclo[3.1.0]-hex-6-yl)ethylaminocarbonyl]naphthyloxy)-2-propanols and methods for preparing these compounds are disclosed. The compounds are useful in the treatment of hypertension and abnormal heart conditions in mammals. These compounds are prepared by the treatment of the corresponding 1,2-epoxy-3-[2-(endobicyclo[3.1.0]hex-6-yl)ethylaminocarbonyl]naphthyloxy)-propane with an alkylamine having the desired alkyl substituent or by base or acid hydrolysis of the corresponding 2-optionally substituted -3-alkyl-5-([2-(endobicyclo[3.1.0]hex-6-yl)ethylaminocarbonyl]naphthyloxymethyl)oxazolidine. These latter compounds can be prepared by condensing a hydroxy-substituted naphthalene with a 3-alkyl-5-tosyloxymethyloxazolidine such substituted or unsubstituted at the 2-position or alternatively, by treating the former aminopropanol compounds of the present invention with an aldehyde having the desired substituent. These latter oxazolidine compounds are also active for treatment of hypertension and abnormal heart conditions.

14 Claims, No Drawings

BICYCLO[3.1.0]HEXYLETHYLAMINOCARBONYL-SUBSTITUTED NAPHTHYLOXY CARDIOVASCULAR AGENTS

FIELD OF INVENTION

The invention relates to 1-alkylamino-3([2-(endobicyclo[3.1.0]hex-6-yl)ethylaminocarbonyl]naphthyloxy-2-propanol, and pharmaceutically acceptable salts thereof and to methods for preparing such compounds. This invention further relates to 2-optionally substituted-3-alkyl-5-[2-(endobicyclo[3.1.0]hex-6-yl)ethylaminocarbonyl]naphthyloxymethyl) oxazolidines, to pharmaceutically acceptable salts thereof and to methods for preparing such compounds. This invention also relates to pharmaceutical compositions comprising one or more of the above compounds and to methods for treating cardiac disorders and hypertension in mammals.

At the present time, the compound most frequently used in the United States for treatment of cardiac arrhythmia and hypertension is 1-(isopropylamino)-3-(1-naphthoxy)-2-propanol (i.e. Propanolol). Propanolol is believed to achieve its therapeutic action by competing with beta-adrenergic receptor stimulating agents for available beta receptor sites. When access to such sites is blocked by propanolol, the chronotropic, inotropic and vasodilator responses to beta-adrenergic stimulation is decreased. Such activity is however not specific. Not only are heart muscle receptor sites affected, but lung and related organs are found to be influenced by this drug. Contraindication is therefore indicated for patients with bronchial asthma, allergic rhinitis, sinus brachycardia and the like.

In order to overcome the disadvantages present in the non-specific beta-adrenergic blocking agents, drugs selective for heart muscle blockage have been developed. See for example U.S. Pat. No. 3,408,387. One of the most active compounds of the selective beta blockers is N-[4-(2-hydroxy-3-[(1-methylethyl)amino]propoxy]acetanilide, e.g. practolol. Unfortunately, this compound exhibits disadvantageous side effects in man.

U.S. Pat. No. 3,897,441 discloses certain 3-(5-substituted aminocarbonylthiazol-2-yloxy)-2-propanol-1-amines and U.S. patent application Ser. No. 706,342 filed July 19, 1976 now U.S. Pat. No. 4,064,258 discloses various 5-carbocyclic alkylaminocarbonylthiazol-2-yloxy compounds. Both these comcompound-types display beta adrenergic blocking activity and cardiac selectivity. A novel analogous class of compounds having surprising blocking activity, cardiac selectivity and reduced cardiac depression has now been discovered. These compounds are especially felicitous for the treatment or palliation of angina pectoris and cardiac arrhythmias and, because of their cardiac selectivity, can be safely applied to patients suffering from asthma or chronic obstructive lung disease.

SUMMARY

In summary, the compounds in accordance with the present invention can be represented by the following generic formula

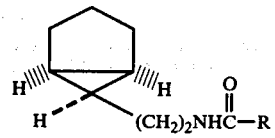
(I)

where R is

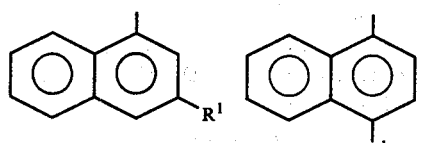

wherein $R^1$ is the radical $-OCH_2CH(OH)CH_2NHR^2$ or

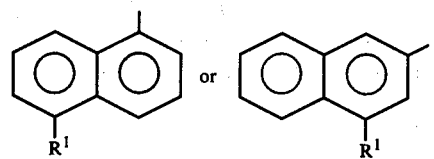

where $R_2$ is $C_1$ to $C_4$ linear or branched alkyl, $R^3$ is hydrogen, $C_1$ to $C_4$ linear or branched alkyl or $C_6$ to $C_{10}$ carbocyclic aryl optionally substituted with halo, $C_1$ to $C_4$ linear or branched alkyl, $C_1$ to $C_4$ linear or branched alkoxy, $C_2$ to $C_4$ linear or branched acyl, nitrile, nitro or $C_1$ to $C_4$ linear or branched carboalkoxy.

Also encompassed within the present invention are pharmaceutically acceptable salts of the above compounds.

The process of preparing the compounds of the present invention where $R^1$ is the radical $-OCH_2CH(OH)CH_2NHR^2$ comprises treating the corresponding 1,2-epoxy-3-([2-(endobicyclo[3.1.0]hex-6-yl)ethylaminocarbonyl]naphthyloxy)propane with an alkylamine having the desired alkyl substituent. Alternatively, the compounds can be prepared by the acid or base hydrolysis of the corresponding compounds of the present invention where $R^1$ is the radical

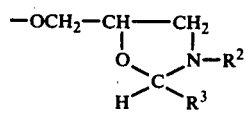

The process of preparing the compounds of the present invention where $R^1$ is the radical

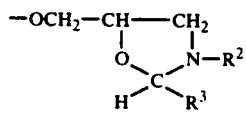

comprises condensing an [(endobicyclo[3.1.0]hex-6-yl)ethylaminocarbonyl]naphthyloxy radical having the hydroxy group at the desired position on the carboxylic aryl ring with a 5-tosyloxymethyloxazolidine having the desired $R^2$ and $R^3$ substiuents or treating the corresponding compounds of the invention where $R^1$ is the radical —$OCH_2CH(OH)CH_2NHR^2$ with the desired $R^3$ aldehyde.

The pharmaceutical compositions of the present invention include both solids or powders and solutions comprising one or more of the compounds of the invention in combination with a suitable pharmaceutical solvent, e.g. sterile water or pharmaceutical solid excipients.

The compounds in accordance with the present invention will be further discribed in the Description of the Preferred Embodiments.

DESCRIPTION OF THE PREFERRED EMBODIMENTS

The carbocyclic aryl compounds in accordance with the present invention are represented by the formula:

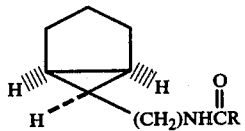

(I)

where R is

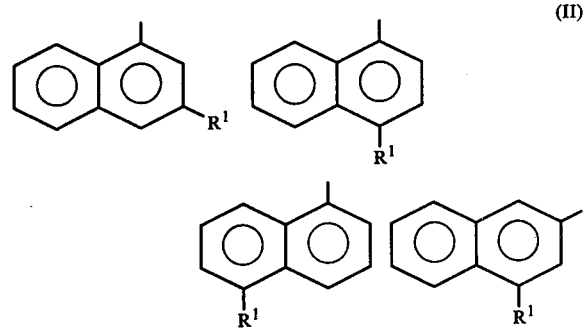

(II)

In the interest of brevity, the above carbocyclic aryl radicals will sometimes be refered to hereinafter as the naphthyl radicals, II. The open bond on the above series II radicals represents the point of attachment to the group

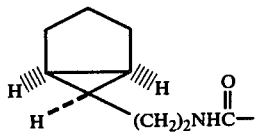

The group $R^1$ in the above series of radicals II is the group

—$OCH_2CH(OH)CH_2NHR^2$ or 

(Ia)             (Ib)

where $R^2$ is $C_1$ to $C_4$ linear or branched alkyl, and $R^3$ is hydrogen, $C_1$ to $C_4$ linear or branched alkyl or $C_6$ to $C_{10}$ carbocyclic aryl optionally substituted with halo, $C_1$ to $C_4$ linear or branched alkoxy, $C_2$ to $C_4$ linear or branched acyl, nitrile, nitro, or $C_1$ to $C_4$ linear or branched carboalkoxy.

It should be understood that, the compounds of the present invention have asymmetric carbon atoms and can therefore exist as optically active isomers. Thus, the above formula is intended to represent the individual (+) or (−) optical isomers as well as the racemic mixtures thereof.

The pharmaceutically acceptable salts of the compounds of Formula I are also embraced by the present invention. By pharmaceutically acceptable salts is meant those pharmaceutically acceptable hydrogen organic or inorganic anion addition salts which do not adversely affect the pharmaceutical properties of the parent compound. Suitable organic anions include, for example acetate, benzoate, lactate, picrate, propionate, butyrate, valerate, tartrate, maleate, fumarate, citrate, succinate, tosylate, ascorbate, nicotinate, adipate, gluconate and the like. Suitable inorganic anions include for example chloride, bromide, iodide, sulfate, phosphate, nitrate and the like.

Typical illustrations of the compounds of the present invention and salts thereof can be had by references to the Examples. Where $R^1$ is —$OCH_2CH(OH)CH_2NHR^2$ the preferred $R^2$ substituents are isopropyl or t-butyl, especially isopropyl.

The particularly preferred compounds in accordance with the present invention where $R^1$ is

—$OCH_2CH(OH)CH_2NHR^2$ are:

1-isopropylamino-3-(3-[2-(endobicyclo[3.1.0]hex-6-yl)-ethylaminocarbonyl]naphth-1-yloxy)-2-propanol;
1-t-butylamino-3-(3-[2-(endobicyclo[3.1.0]hex-6-yl)-ethylaminocarbonyl]naphth-1-yloxy)-2-propanol;
1-isopropylamino-3-(4-[2-(endobicyclo[3.1.0]hex-6-yl)-ethylaminocarbonyl]naphth-1-yloxy)-2-propanol;
1-t-butylamino-3-(4-[2-endobicyclo[3.1.0]hex-6-yl)-ethylaminocarbonyl]naphth-1-yloxy)-2-propanol;
1-isopropylamino-3-(5-[2-(endobicyclo[3.1.0]hex-6-yl)-ethylaminocarbonyl]naphth-1-yloxy)-2-propanol;
1-t-butylamino-3-(5-[2-(endobicyclo[3.1.0]hex-6-yl)-ethylaminocarbonyl]naphth-1-yloxy)-2-propanol;
1-isopropylamino-3-(4-[2-(endobicyclo[3.1.0]hex-6-yl)-ethylaminocarbonyl]naphth-2-yloxy)-2-propanol;
1-t-butylamino-3-(4-[2-(endobicyclo[3.1.0]hex-6-yl)-ethylaminocarbonyl]naphth-2-yloxy)-2-propanol;

The preferred compounds of the present invetion where $R^1$ is

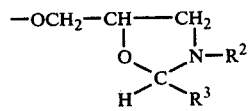

are $R^2$ being isopropyl or t-butyl. In the case of $R^3$ the aromatic substituents are preferred, such being $C_6$ to $C_{10}$ carbocyclic aryl preferably phenyl optionally substituted with preferably halo, methyl, methoxy, acetoxy, nitrile or nitro.

The particularly preferred compounds in accordance with the present invention where R¹ is

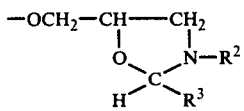

are:

2-phenyl-3-isopropyl-5-(4-[2-(endobicyclo[3.1.0]hex-6-yl)ethylaminocarbonyl]naphth-1-yloxymethyl)oxazolidine, 2-phenyl-3-t-butyl-5-(4-[2-(endobicyclo[3.1.0]hex-6-yl)ethylaminocarbonyl]naphth-1-yloxymethyl)oxazolidine and the like.

The preferred pharmaceutically acceptable salts are the hydrogen addition salts of the bromide, sulfate, lactate, tartrate, succinate, and especially chloride and maleate. The preferred salts are the preferred anion addition salts of the compounds in accordance with the present invention and correspondingly the particularly preferred salts are the preferred hydrogen-anion addition salts of the preferred and particularly preferred compounds herein, and especially the hydrochloride and maleate salts.

The compounds in accordance with the present invention are conveniently prepared by applying many of the procedures disclosed in the before referenced U.S. patent application Ser. No. 706,412, filed July 19, 1976, now U.S. Pat. No. 4,064,135. Particularly, the compounds of the present invention where R¹ is —OCH₂CH(OH)CH₂NHR² and R is

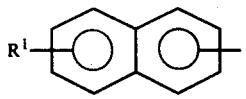

wherein R¹ is at the naphthyl ring position 1 or 2 and the open bond, i.e., the point of attachment to the group 2-(endobicyclo[3.1.0]hex-6-yl)ethylaminocarbonyl is at ring position 3, 4 or 5 are readily prepared from the corresponding 1,2-epoxy-3-(1 or 2-naphthyloxy)propanes substituted at the desired ring position with the 2-(endobicyclo[3.1.0]hex-6-yl)ethylaminocarbonyl group. Illustrative of the reaction path for obtaining the naphthyl compounds of the present invention is the reaction sequence set forth below:

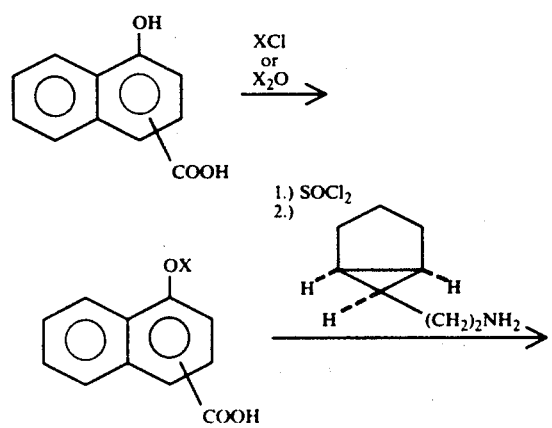

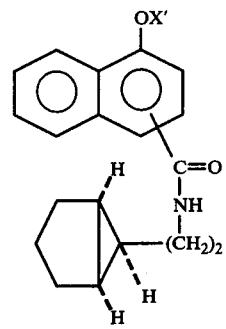

where X is C₂ to C₄ linear or branched acyl.

The above amide-forming raction can be carried out by any of the well-known classical prior art procedures. Most conveiently, the amide is formed by first admixing the carboxylic acid with thionyl chloride in an aromatic solvent and heating to a temperature of about 70° C. The amine can then be added without isolating the intermediate acid chloride, giving the amide, compound III. See for example Preparation 4a.

In some cases, it is more convenient to prepare the amide (precursor compound III), via a mixed anhydride, by directly reacting the naphthoic acid with an alkyl haloformate followed by the addition of 2-(endobicyclo[3.1.0]hex-6-yl)ethylamine. See for example Preparation 4b. The compounds in accordance with the present invention are prepared from the above precursor compound III by the following reaction scheme:

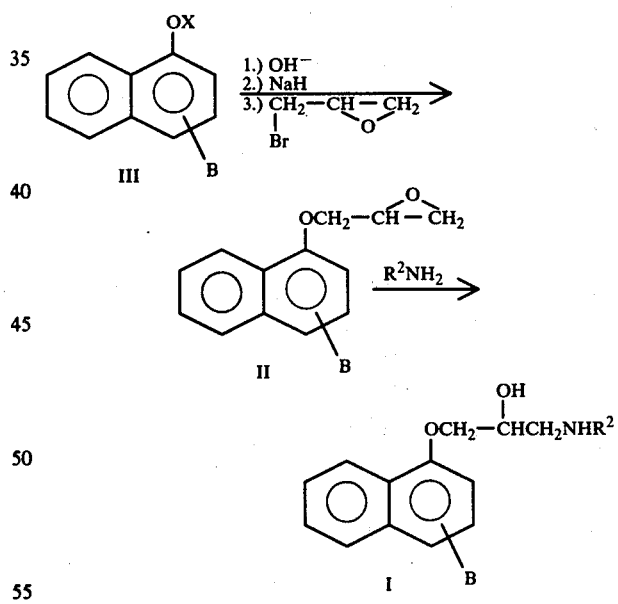

where X and R² are defined above and B is the group

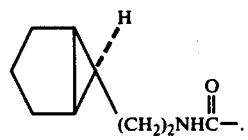

The formation of the oxirane adduct e.g., compound II is specifically illustrated herein in Preparation 6.

The above sequence can be effected by first treating the compound of formula III with strong base such as aqueous sodium hydroxide to remove the protecting group X. The resulting naphthol (i.e. where X = H in compound III) is then typically reacted with an alkali metal hydride. This initial treatment is typically conducted at temperatures in the range of about from −30° to 30° C., preferably from about −10° to 5° C. for from about one minute to one hour, preferably from about five minutes to 20 minutes. An epihalohydrin such as epibromohydrin or epichlorohydrin typically dissolved in an inert organic solvent, is then added to the preceding mixture. Typically, this treatment is conducted at temperatures in the range of from about 25° to 45° C., for from about one minute to three hours, preferably from about 10 to 30 minutes. Typically, mole ratios of alkali metal hydride:naphthol [i.e. where X = H in compound III] of from about 1 to 5:1 are used, preferably from about 1.0 to 1.3:1, and mole ratios of compound of formula III (i.e. where X = H):epihalohydrin in the range of from about 1 to 5:1 preferably from about 1.0 to 1.3:1 are used. Suitable alkali metal hydrides which can be used include, for example, sodium hydride, potassium hydride, lithium hydride, and the like. Suitable inert organic solvents which can be used include, for example, tetrahydrofuran, diethyl ether, dioxane, dimethoxyethane, dimethylformamide and the like, and mixtures thereof. Both procedures of the treatment are conducted under anhydrous conditions, and preferably under an inert atmosphere (e.g. nitrogen). Intermediate compound II is preferably isolated before being used as starting material for the next step. Such isolation can be effected by conventional separation procedures such as, for example, precipitation with water, extraction, crystallization or chromatography. Specific illustrations of typical separation and isolation procedures can be had by reference to the appropriate Preparations, hereinbelow.

The compounds of the present invention having the substituent Ia can be conveniently prepared by treating compound II with a monoalkylamine having the desired alkyl substituent. Typically, this treatment is conducted in an inert organic solvent and is typically conducted at temperatures in the range of from about −10° to 100° C., preferably from about 10° to 50° C., for from about one hour to 48 hours, preferably from about three to 18 hours. Typically, a mole ratio of alkylamine:compound II is in the range of from about one to 30:1, preferably from about one to 10:1, is used. Suitable alkylamines which can be used include, for example, methylamine, ethylamine, isopropylamine, t-butylamine, and the like. Suitable inert organic solvents which can be used include, for example, methanol, ethanol, monoglyme, and the like and mixtures thereof. The resulting products bearing the substituent Ia can then be separated and isolated according to conventional procedures such as, for example, evaporation, crystallization, chromatography, thin-layer chromatography, etc. Specific illustrations of typical separation and isolation procedures can be had by reference to the corresponding Examples, set forth hereinbelow.

The compounds of the present invention bearing the substituent Ib can be prepared directly from the correponding compounds having the substituent Ia as follows:

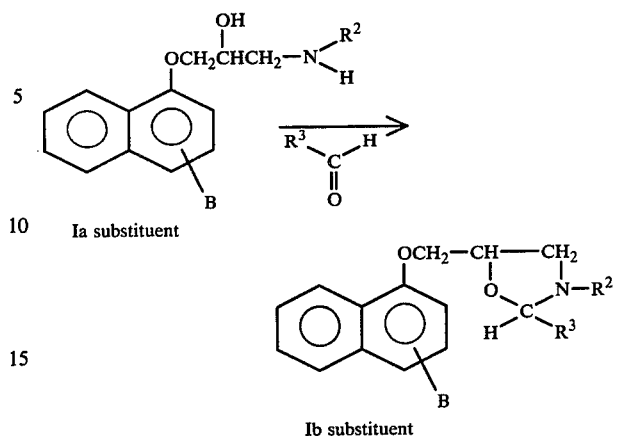

wherein $R^2$, $R^3$, and B are as defined hereinabove.

This preparation can be conveniently effected by treating the corresponding compound bearing the substituent Ia with an aldehyde having the desired $R^3$ substituent. The reaction can be carried out by simply treating the compound of substituent Ia with the desired aldehyde using a lower alkanol (e.g. ethanol) as solvent. Typically a mole ratio of from about one to 10 moles of aldehyde is used per mole of compound of substituent Ia. The reactions are typically conducted at temperatures in the range of from about 20° to 140° C. for from about one to 48 hours. Suitable aldehydes which can be used include, for example formaldehyde, acetaldehyde, benzaldehyde, p-acetylbenzaldehyde, p-cyanobenzaldehyde, p-chlorobenzaldehyde, p-carbomethoxybenzaldehyde and the like. In some cases, a strong base is desirably present in the reaction mixture such as aluminum isopropoxide and the like. Alternately, these compounds are prepared by heating a mixture of the desired $R^3$ aldehyde and the compounds of the present invention bearing the substituent Ia in an inert organic solvent such as benzene, toluene, etc. and azeotropically removing water.

Alternatively, the oxazolidine compounds in accordance with the present invention bearing the substituent Ib can be prepared by the following reaction:

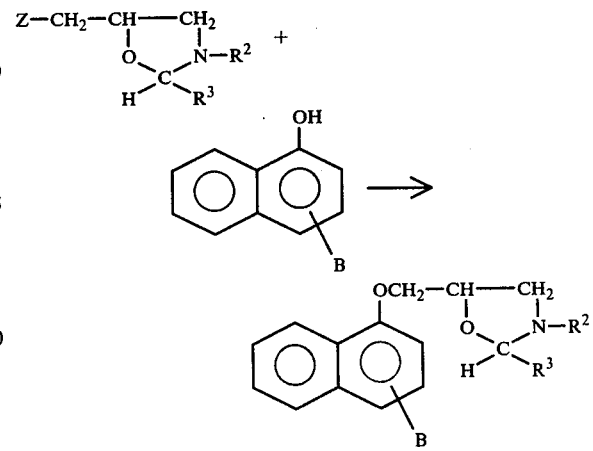

where Z is any readily displaceable group such as halo, mesyloxy, tosyloxy and the like and B, $R^2$ and $R^3$ are described above.

This reaction is conveniently carried out by first treating the 5-hydroxymethyl-3-alkyl 2-optionally substituted oxazolidine with a reagent that will react with the hydroxy moiety of the 5-hydroxymethyl group thereby forming an intermediate bearing a 5-methyl-leaving group-substituted oxazolidine (the group Z). Such displaceable leaving groups are well known in the prior art, e.g., the reactions of alcohols with the selected reagents to yield leaving group-substituted intermediates. See for example Fieser & Fieser, Reagents for Organic Synthesis, page 662 (1967) and Example 7 herein. Preferably the leaving group Z is tosyloxy or mesyloxy. After isolation of the Z-substituted oxazolidine by any conventional prior art technique, the displacement is affected by subsequent reaction with the desired B substituted naphthol anion to yield the oxazolidine compound of substituent Ib. Typically, the leaving group-substituted oxazolidine is formed by reaction of methanesulfonyl chloride or p-toluenesulfonylchloride with the oxazolidine alcohol in the presence of an acid acceptor-containing solution. Typical acid acceptors are the trialkyl- or arylamines or alkali metal carbonates. The subsequent reaction with the naphthol is accomplished by first activating the naphthol typically with an alkali metal hydride such at temperatures of about $-10°$ to about $100°$ preferably $0°$ to $30°$ C. for about one minute to about 1 hour preferably five minutes to 20 minutes. The oxazolidine dissolved in a organic solvent is next added and the mixture is heated at from about $25°$ to about $100°$ C. preferably $70°$ to $90°$ C. for about 1 hour to about 8 hours preferably 1 hour to 3 hours. Typically the ratio of 5-hydroxymethyl-substituted oxazolidine: leaving group reagent is in the range 1 to 5:1, preferably 1 to 1.5:1. The ratio of 5-leaving group-substituted oxazolidine: B substituted alpha or beta naphthol: alkali metal hydride is in the range 1 to 5:1:1 to 2 preferably 1.3:1:1.1.

The product of substituent Ib can be separated and purified according to conventional procedures such as, for example, illustrated in Example 4, hereinbelow. Care should be exercised during the purification procedure as the compounds of substituent Ib are easily hydrolyzed to the compounds of substituent Ia under both acid and basic conditions. The alkylamino compounds having the substiuent Ia can be readily prepared by simple acid or base hydrolysis of the corresponding compounds of substituent Ib. Acid hydrolysis can be conveniently effected by treating the compound of substituent Ib with a suitable organic acid such as, for example, acetic acid, formic acid, oxalic acid and the like or a suitable inorganic acid such as, for example, hydrochloric acid, sulfuric acid and the like. Preferably this hydrolysis is conducted under mildly acidic conditions. Similarly, basic hydrolysis can be conducted by treating the compounds of substituent Ib with a suitable base such as, for example, dilute sodium hydroxide. Preferably this hydrolysis is conducted under mildly alkaline conditions. Alternatively, the hydrolysis can be conducted via exchange with a suitable ion exchange resin in either the $H^+$ or $OH^-$ form.

The pharmaceutically acceptable acid addition salts of the compounds of the present invention bearing the substituents Ia or Ib can be prepared from the parent compounds, via careful neutralization, with the desired acid. Other pharmaceutically acceptable addition salts can then be conveniently prepared from the addition salts via anion exchange with a suitable ion exchange resin in the desired anionic form.

The compounds of the invention are useful in the treatment and palliation or cardiovascular abnormalities in mammals. These compounds primarily achieve their therapeutic action by selectively blocking the cardiac betaadrenergic receptor sites and, accordingly, because they are cardiac selective, they can also be applied to treat cardiac abnormalities in patients suffering from asthma or chronic obstructive lung disease.

The compounds are especially useful in the treatment or palliation of cardiac arrhythmias, angina pectoris, hypertrophic subaortic stenosis, pheochromocytoma, thyrotoxicosis, hyperkenetic syndromes, tetralogy of Fallot, mitral stenosis with tachycardia, general ischemic conditions, and hypertension founded on elevated cardiac outputs due to a hyperadrenergic state. The compounds are active, both in the treatment or palliation of acute attacks of such cardiac disorders, and further can be applied prophylactically to prevent or reduce the frequency of such attacks. This prophylactic action is particularly desirable in reducing the frequency of attacks of angina pectoris, since the medication presently commonly used (i.e. nitroglycerin) in the treatment of angina pectoris has no recognized prophylactic action. Additional information concerning the use, action and determination of beta-blockers can be obtained by reference to the literature such as, for example, Dotlery et al., Clinical Pharmacology and Therapeutics, Volume 10, No. 6, 765–797 and the references cited therein.

The compounds of the invention are also useful in the treatment of hypertension in mammals.

The compounds of this invention are typically administered, both for the treatment of cardiac disorders and hypertension, in dosages of about from 0.01 to 5 mg per kg. of body weight. The precise effective dosage will, of course, vary depending upon the mode of administration, the condition being treated and the host. Where the compounds are used to treat cardiac conditions such as arrhythmias, the compounds are typically administered either orally or intravenously. Where the compounds are administered to treat hypertension or cardiac conditions such as angina pectoris, the compounds are, for the sake of convenience, typically administered orally.

The compounds of the invention can be administered for the treatment of cardiac disorders and hypertension in a wide variety of dosage forms, either alone or in combination with other pharmaceutically compatible medicaments, in the form of pharmaceutical compositions suited for oral or parenteral administration. The compounds are typically administered as pharmaceutical compositions consisting essentially of the compounds of the invention and a pharmaceutical carrier. In the case of the compounds of formula Ia, the compounds are typically administered as pharmaceutically acceptable salts. The pharmaceutical carrier can be either a solid material or liquid, in which the compound is dissolved, dispersed or suspended, and can optionally contain small amounts of preservatives and/or pH-buffering agents. Suitable preservatives which can be used include, for example, benzyl alcohol and the like. Suitable buffering agents include, for example, sodium acetate, pharmaceutical phosphate salts and the like.

The liquid compositions can, for example, be in the form of solutions, emulsions, suspensions, syrups, or elixirs and optionally can contain small quantities of preservatives and/or buffering agents, and preferably contain the therapeutic agent in convenient unit dosage concentrations.

The solid compositions can take the form of tablets, powders, capsules, pills or the like, preferably in unit dosage forms for simple administration or precise dosages. Suitable solid carriers include, for example, pharmaceutical grades of starch, lactose, sodium saccharine, sodium bisulfite and the like.

Also based on studies on related compounds, it can be predicted that a number of the present compounds will exhibit useful local anesthetic activity. Where the compounds are applied as local anesthetics, they can be administered topically, intradermally, or subcutaneously.

A further understanding of the invention can be had from the following non-limiting Preparations and Examples. Also as used hereinabove and below unless expressly stated to the contrary, all temperatures and temperature ranges refer to the Centrigrade system and the terms ambient or room temperature refer to about 20° C. The term percent or (%) refers to weight percent and the term mole or moles refers to gram moles. The term equivalent refers to a quantity of reagent equal in moles to the moles of the preceding or succeeding reactant recited in that Preparation or Examples in the terms of moles of finite weight or volume. Proton or $^{13}$carbon nuclear magnetic reasonance spectra (NMR and $^{13}$C NMR) are determined at 100, 90, or 60 MHz (the signs of the coupling constants are not assigned) and signals are assigned as singlets (s), broad singlets (bs) doublets (d), double doublets (dd), triplets (t), double triplets (dt), quartets (q) and multiplets (m) and reported using the delta scale from tetramethylsilane (internal standard) unless otherwise noted. Compounds having assymetric centers and optical activity are isolated in their racemic form (±) unless otherwise indicated.

PREPARATION 1

2-(Endobicyclo[3.1.0]hex-6-yl)ethylamine a. In this prepration 1.9 g. (0.05 mole) of lithium aluminum hydride is dissolved in 100 ml. of diethyl ether, under nitrogen, cooled to 0° C., and then 10.8 g. (0.1 mole) of endobicyclo[3.1.0]hex-2-en-6-yl carboxaldehyde in 100 ml. of diethyl ether is added dropwise. The mixture is allowed to warm to room temperature, and then stirred for 30 minutes. Ten milliliters of ethyl acetate is added, and then 10 ml. of water. The mixture is filtered and the filtrate dried with anhydrous magnesium sulfate, filtered, and the filtrate evaporated under vacuum affording 6-(hydroxymethyl)endobicyclo[3.1.0]hex-2-ene.

b. A mixture containing 10 g. (0.091 mole) of 6-(hydroxymethyl)endobicyclo[3.1.0]hex-2-ene and 0.5 g. of 5% platinum on carbon in 250 ml. of ethyl acetate is stirred under hydrogen, at room temperature, until no further hydrogen is absorbed (about two liters is absorbed). The catalyst is removed by filtration and the filtrate evaporated under vacuum affording 6-(hydroxymethyl)endobicyclo[3.1.0]hexane.

c. Ten grams (0.089 mole) of 6-(hydroxymethyl)endobicyclo[3.1.0]hexane is mixed with 23.4 g. (0.089 mole) of triphenylphosphine in 40 ml. of carbon tetrachloride and heated, under nitrogen, at 60° C. for four hours. The mixture is poured into 200 ml. of hexane, stirred, and then filtered, the filtrate concentrated by evaporation under vacuum. The concentrate is then chromatographed on silica gel, eluting with 5% ethyl acetate - 95% (vol.) hexane, affording 6-(chloromethyl)endobicyclo[3.1.0]hexane.

d. A mixture containing 9 g. (0.069 mole) of 6-(chloroethyl)endobicyclo[3.1.0]hexane and 4.9 g. (0.1 mole) of sodium cyanide in 100 ml. of dimethylsulfoxide is heated at 70° C., under nitrogen, for four hours, and then poured into 500 ml. of methylene chloride. The mixture is washed three times with water, dried over anhydrous magnesium sulfate, and filtered. The filtrate is evaporated under vacuum and the resulting residue chromatographed on silica gel, eluting with 5% ethyl acetate - 95% (vol.) hexane affording endobicyclo[3.1.0]-hex-6-yl acetonitrile.

e. 2.2 Grams (0.058 mole) of lithium aluminum hydride is dissolved in 100 ml. of anhydrous diethyl ether at 0° C., under nitrogen, and 7 g. (0.058 mole) of endobicyclo[3.1.0]hex-6-yl acetonitrile in 100 ml. of diethyl ether is added dropwise. The mixture is maintained at 0° C. for 30 minutes and 10 ml. of water carefully added. The resulting mixture is filtered, the filtrate is dried over potassium hydroxide pellets, filtered again, and the filtrate distilled to remove the ethyl ether solvent, affording 2-(endobicyclo[3.1.0]hex-6-yl)ethylamine.

PREPARATION 2 a. 1-Acetoxy-3-naphthoic acid

To a suspension of 2.3 g. of 4-hydroxy-1-naphthoic acid in 100 ml. of methylene chloride and 100 ml. of tetrahydrofuran, a mixture of 1.5 g. of triethylamine, 1.6 g. of 4-N-dimethylaminopyridine and 1.5 g. of acetic anhydride is added. The reaction mixture is heated at 50° for one hour. The solution is extracted with ethyl acetate, the organic layer washed with water and dilute hydrochloride acid and evaporated to dryness to yield 2.1 g. of the acetoxy carboxylic acid.

b. 1-Acetoxy-5-naphthoic acid

A solution of 20 g. of 5-hydroxy-1-naphthoic acid in 200 ml. of benzene and 40 ml. of acetyl chloride is refluxed for 3 hours. Solvent and excess acetyl chloride are evaporated. The mixture is dissolved in methanol (150 ml.) and water (20 ml.) added. After 15 minutes, addition of more water results in the precipitation of 1-acetoxy-5-naphthoic acid.

Similarly prepared is 2-acetoxy-4-naphthoic acid.

PREPARATION 3

1-Acetoxy-4-Naphthoic Acid

To 1-acetoxy-4-naphthaldehyde (2.5 g.) in 150 ml. of acetone at 5°, 8 ml. of Jones reagent are added during 30 minutes. The mixture is allowed to warm to room temperature and stirring is continued for an additional 40 minutes. Thereafter, any excess of the Jones reagent is reduced by the addition of isopropyl alcohol and the solvent is evaporated (in vacuo). The acid is precipitated with water, collected by filtration and dried, affording 2.2 g. of 1-acetoxy-4-naphthoic acid, m.p. 182°-184°.

PREPARATION 4 a. 4-[2-(Endobicyclo[3.1.0]hex-6-yl)ethylcarbonyl]-2-naphthyl acetate

A mixture of 15 ml. of thionyl chloride, 2.15 g. of 3-acetoxy-1-naphthoic acid (Preparation 3) in 150 ml. of benzene is stirred at 70° for 3 hours under nitrogen, the solvent removed under vacuum. The residue is dissolved in dry tetrahydrofuran (150 ml.) and a mixture of triethylamine (3 ml.) and 2-(endobicyclo[3.1.0]hex-6- yl)ethylamine (1.38 g., 0.011 mole) is added dropwise with stirring at room temperature. After stirring for 2 hours, the mixture is poured into ethyl acetate (300 ml.), washed twice with a saturated sodium chloride solution, dried over magnesium sulfate, filtered and the solvent removed under vacuum. After chromatographing the residue on silica gel and eluting with 50% ethyl acetate - 50% hexane, the acetate is isolated, yielding 1.6 g. of
4-[2-(endobicyclo[3.1.0]hex-6-yl)ethylaminocarbonyl]-2-naphthyl acetate.

Similarly by following the same procedure above but using the other acetoxy naphthoic acids illustrated in Preparation 2 the following are prepared:
5-[2-(endobicyclo[3.1.0]hex-6-yl)ethylaminocarbonyl]-1-naphthyl acetate.
3-[2-(endobicyclo[3.1.0]hex-6-yl)ethylaminocarbonyl]-1-naphthyl acetate.

b. 4-[2-(Endobicyclo[3.1.0]hex-6-yl)ethylaminocarbonyl]-1-naphthyl acetate

1-Acetoxy-4-naphthoic acid (2.1 g.) is dissolved in tetrahydrofuran (20 ml.), and triethylamine (1.3 g.) is added. The components are allowed to stir for five minutes at 5° C. and then ethylchloroformate (1.4 g.), is added. After 30 minutes at 5° C., 2-(endobicyclo[3.1.0-]hex-6-yl)ethylamine (1.5 g.) is added and the reaction is kept at 5° C. for 15 additional minutes. The solution is then heated at reflux for 15 minutes. The tetrahydrofuran is evaporated (vacuum) and the residue is taken up in diethyl ether (20 ml.). The ether solution is washed with 5% aqueous sodium bicarbonate, water, 5% aqueous hydrochloric acid and water. After drying over anhydrous magnesium sulfate, the solution is filtered and evaporated to dryness (in vacuo) affording 1.6 g. of the captioned compound ---
$^1$H NMR in CDCl$_3$
0.6 – 2.0 (m, 11H, CH and CH$_2$)
2.48 (s, 3H, —OCOCH$_3$)
3.60 (q, 2H, J=7.0 Hz, NCH$_2$)
6.20 (broad, 1H, CONH)
7.27, 7.60, 7.95, 8.35 (m, 6H, aromatic H).
---

PREPARATION 5

4-[2-(endobicyclo[3.1.0]hex-6-yl)ethylaminocarbonyl]-1-naphthol

A mixture of 1.5 g. of the acetate of Preparation 4 in 10 ml. of methanol, 3.0 g. of sodium hydroxide in 20 ml. of water, is heated for 3 minutes at 60° C. After cooling, 30 ml. of water are added and the mixture is extracted with ether (2 × 100 ml.). The aqueous layer is made acidic (ca. pH 2) with 10% hydrochloric acid and extracted with ether (3 × 100 ml.), dried over anhydrous magnesium sulfate, filtered and the solvent removed to yield the solid naphthol product, 1.1 g.

Similarly, by following the same procedure above but using the substituted naphthyl acetate illustrated in Preparation 4, the following compounds are prepared:
3-[2-(endobicyclo[3.1.0]hex-6-yl)ethylaminocarbonyl]-1-naphthol;
5-[2-(endobicyclo[3.1.0]hex-6-yl)ethylaminocarbonyl]-1-naphthol;
4-[2-(endobicyclo[3.1.0]hex-6-yl)ethylaminocarbonyl]-2-naphthol.

PREPARATION 6

1,2-Epoxy-3-(4-[2-(endobicyclo[3.1.0]hex-6-yl)ethylaminocarbonylnaphth-1-yloxy]propane To a solution of sodium hydride (400 mg.) in 5 ml. of anhydrous methanol is added a solution of the naphthol of Preparation 5 in 5 ml. of anhydrous methanol. Benzene (200 ml.) is added and the solvents are distilled to near dryness, and then 100 ml. of benzene is added and distillation to near dryness is repeated. The last traces of solvent are removed in vacuo, and to the residue is added 20 ml. of dry tetrahydrofuran, 10 ml. of dry dimethylformamide and 2.3 g. of epichlorohydrin. The mixture is heated at 75° C. for 2½ hours, cooled and the solvents removed by evaporation (in vacuo). Diethyl ether (150 ml.) and ethyl acetate (50 ml.) are added to the residue and the resulting solution is washed with an equal volume of water, dried over magnesium sulfate, filtered and evaporated to dryness (in vacuo) to give the entitled compound (1.0 g., solid). Recrystallization from methylene chloride/ether gave a pure crystalline product, m.p. 105°–107° C.

Similarly, by following the same procedure above but using other substituted naphthols, the following compounds are prepared:
1,2-epoxy-3-(3-[2-(endobicyclo[3.1.0]hex-6-yl)ethylaminocarbonyl]naphth-1-yloxy)propane;
1,2-epoxy-3-(5-[2-(endobicyclo[3.1.0]hex-6-yl)ethylaminocarbonyl]naphthyl-1-yloxy)propane;
1,2-epoxy-3-(4-[2-(endobicyclo[3.1.0]hex-6-yl)ethylaminocarbonyl]naphth-2-yloxy)propane.

EXAMPLE 1

1-Isopropylamino-3-(4-[2-(endobicyclo[3.1.0]hex-6-yl)-ethylaminocarbonyl]naphth-1-yloxy)-2-propanol.

To 900 mg. of the compound illustrated in Preparation 5 in 10 ml. methanol is added 5 ml. of isopropylamine, and the mixture is stirred at room temperature for 24 hours. The above captioned compound, after removal of methanol and excess amine by evaporation (in vacuo) is isolated as a solid (900 mg.) which is crystallized from methanol/ether, m.p. 139°–141° C.

Using the same procedure as above but substituting the other epoxides illustrated in Preparation 6 the following are prepared:
1-isopropylamine-3-(3-[2-(endobicyclo[3.1.0]hex-6-yl)-ethylaminocarbonyl]naphth-1-yloxy)-2-propanol;
1-isopropylamine-3-(5-[2-(endobicyclo[3.1.0]hex-6-yl)-ethylaminocarbonyl]naphth-1-yloxy)-2-propanol;
1-isopropylamine-3-(4-[2-(endobicyclo[3.1.0]hex-6-yl)-ethylaminocarbonyl]naphth-2-yloxy)-2-propanol.

Using the same procedure as above, but substituting t-butylamine for isopropylamine, the following are prepared:
1-t-butylamino-3-(3-[2-(endobicyclo[3.1.0]hex-6-yl)-ethylaminocarbonyl]naphth-1-yloxy)-2-propanol;
1-t-butylamino-3-(4-[2-(endobicyclo[3.1.0]hex-6-yl)-ethylaminocarbonyl]naphth-1-yloxy)-2-propanol;
1-t-butylamino-3-(5-[2-(endobicyclo[3.1.0]hex-6-yl)-ethylaminocarbonyl]naphth-1-yloxy)-2-propanol;
1-t-butylamino-3-(4-[2-endobicyclo[3.1.0]hex-6-yl)-ethylaminocarbonyl]naphth-2-yloxy)-2-propanol.

EXAMPLE 2

This Example illustrates methods of preparing hydrochloride addition salts of the compounds of the present invention having the substituent of formula Ia. In this Example 1 g. of 1-isopropylamino-3-(4-[2-(endobicyclo[3.1.0]hex-6-yl)ethylaminocarbonyl]naphth-1-yloxy)-2-propanol is dissolved in 10 ml. of ethyl ether at 20° C. A stream of gaseous anhydrous hydrogen chloride is passed over the surface of the solution until the supernatent liquid becomes colorless. The resulting precipitate is collected by filtration, washed with diethyl ether and then crystallized from methanol/diethyl ether, affording crystalline 1-isopropylamino-3-(4-[2-(endobicyclo[3.1.0]hex-6-yl)ethylaminocarbonyl]naphth-1-yloxy)-2-propanol hydrochloride.

Similarly, by following the same procedure, the corresponding hydrochloride addition salts of each of the products of Example 1 are respectively prepared.

EXAMPLE 3

This Example illustrates methods of preparing the maleate addition salts of the compounds of the present invention having the substituent of formula Ia. In this Example 1 g. of 1-isopropylamino-3-(4-[2-(endobicyclo[3.1.0]hex-6-yl)ethylaminocarbonyl]naphth-1-yloxy)-2-propanol is dissolved in a solution of 5 ml. of diethyl ether and 5 ml. of ethanol at 20° C. To this solution is added 10 ml. of a saturated solution of maleic acid in ethyl ether. The mixture is allowed to stand for one hour at room temperature. The resulting precipitate is recovered by filtration, washed three times with diethyl ether and then crystallized from a mixture of diethyl ether and ethanol affording crystalline 1-isopropylamino-3-(4-[2-(endobicyclo[3.1.0]hex-6-yl)ethylaminocarbonyl]naphth-1-yloxy)-2-propanol maleate.

Similarly, by following the same procedure, the corresponding maleate salts of each of the products of Example 1 are prepared.

EXAMPLE 4

This Example illustrates the method of converting the compounds where $R^1$ is the substituent Ia into the corresponding compounds where $R^1$ is the substituent Ib. In this Example, 1 mmole of 1-isopropylamino-3-(4-[2-(endobicyclo[3.1.0]hex-6-yl)ethylaminocarbonyl]naphth-1-yloxy)-2-propanol in 10 ml. of methanol is admixed with 20 ml. of acetaldehyde and 2 g. aluminum isopropoxide and then stirred at room temperature for one hour. The solvent is then removed by evaporation under vacuum affording 2-methyl-3-isopropyl-5-(4-[2-(endobicyclo[3.1.0]hex-6-yl)-ethylaminocarbonyl]-naphth-1-yloxymethyl)oxazolidine.

Similarly by following the same procedure but using other aldehydes in place of acetaldehyde, the corresponding 2-substituted 3-isopropyl-oxazolidine analogs of the above products are respectively prepared. By replacing the above compound where $R^1$ is the substituent Ia with other compounds of the present invention where $R^1$ is substituent Ia, other 2-substituted oxazolidine compounds can be prepared with various 2 and 3 substitutions on the oxazolidine ring.

EXAMPLE 5

This Example illustrates the method of converting the compounds bearing the group Ib into the compounds bearing the group Ia of the invention. In this Example, 1 g. of 2-phenyl-3-t-butyl-5-(4-[2-(endobicyclo[3.1.0]hex-6-yl)ethylaminocarbonyl]naphth-1-yloxymethyl)oxazolidine is dissolved in 50 ml. of ethyl acetate and this solution is treated with aqueous 5% sodium hydroxide (20 ml.) at 20° C. The mixture is allowed to stand with intermitant shaking for 0.5 hours, washed three times with water, dried over magnesium sulfate and then evaporated to dryness, affording 1-t-butylamino-3-(4-[2-(endobicyclo[3.1.0]hex-6-yl)ethylaminocarbonyl]naphth-1-yloxy)-2-propanol.

Similarly, by following the same procedures, the products of Example 4 are respectively hydrolyzed to the corresponding compounds having the substituent Ia.

EXAMPLE 6

This Example illustrates an alternate method for converting the compounds having the substituent Ib to the compounds having the substituent Ia. In this Example 1 g. of 2-phenyl-3-t-butyl-5-(4-[2-(endobicyclo[3.1.0]hex-6-yl)-ethylaminocarbonyl]naphth-1-yloxymethyl)oxazolidine is dissolved in 20 ml. of methanol containing 4 ml. of 5% aqueous hydrochloric acid at 20° C. After 15 minutes, the mixture is neutralized with dilute aqueous sodium carbonate solution, poured into water and extracted with ethyl acetate. The ethyl acetate extract is evaporated to dryness yielding 1-t-butylamino-3-(4-[2-(endobicyclo[3.1.0]hex-6-yl)ethylaminocarbonyl]-naphth-1-yloxy)-2-propanol.

Similarly, by following the same procedure, the products of Example 4 are respectively hydrolyzed to the corresponding compounds of substituent Ia.

EXAMPLE 7

This Example illustrates an alternate method for the preparation of the compounds of the present invention having the substituent Ib.

2-Phenyl-3-t-butyl-5-(4-[2-(endobicyclo[3.1.0]hex-6-yl)-ethylaminocarbonyl]naphth-1-yloxymethyl)oxazolidine.

a. 2-phenyl-3-t-butyl-5-p-toluenesulfonyloxymethyloxazolidine.

To a solution of 2-phenyl-3-t-butyl-5-hydroxymethyloxazolidine (12.05 g.) in triethylamine (120 ml.) is added p-toluenesulfonylchloride (14.5 g.). After 6 days at room temperature the mixture is added to water (500 ml.) and extracted with diethyl ether (2 × 200 ml.). The diethyl ether solution is washed with water, dried with anhydrous magnesium sulfate and evaporated to dryness. The residue is recrystallized from hexane to afford 5.4 g. of 2-phenyl-3-t-butyl-5-p-toluenesulfonyloxymethyloxazolidine.

Also prepared by the above technique, but substituting the desired oxazolidine for 2-phenyl-3-t-butyl-5-p-toluenesulfonyloxymethyloxazolidine are:

3-t-butyl-5-p-toluenesulfonyloxymethyloxazolidine, m.p. 69°-70° C.; and 2-methyl-3-t-butyl-5-p-toluenesulfonyloxymethyloxazolidine.

b. A sodium hydride (57%) dispersion in mineral oil (90 mg.) is washed with pentane 3 times, and treated with 5 ml. of dry DMF. To the resulting dispersion is added 590 mg. of 4-[2-(endobicyclo[3.1.0]hex-6-yl)ethylaminocarbonyl]-1-naphthol dissolved in 15 ml. of DMF. After 10 minutes, 782 mg. of 2-phenyl-3-t-butyl-5-p-toluenesulfonyloxymethyloxazolidine (step a) in 5 ml. of DMF are added and the temperature of the reaction mixture raised to approximately 80° C. Stirring is continued for 2 hours. The reaction mixture is cooled, poured into 50 ml. of water, and extracted with 75 ml. of methylene chloride (three times). The combined organic layers are washed with an equal volume of water, dried over sodium sulfate, and evaporated to dryness to give the above titled oxazolidine. Purification is accomplished by column chromatography on silica gel, eluting with ethyl acetate/hexane (1:2 v/v).

EXAMPLE 8

This Example illustrates a further method of converting the compounds having the substituent Ia into the corresponding compounds having the substituent Ib. In this Example 1 mmole of 1-isopropylamino-3-(4-[2-(endobicyclo[3.1.0]hex-6-yl)ethylaminocarbonyl]naphth-1-yloxy)-2-propanol in 10 ml. of methanol is admixed with 20 ml. of 37% aqueous formaldehyde and then stirred at room temperature for one hour. The solvent is then removed by evaporation under vacuum affording a crude 3-isopropyl-5-(4-[2-endobicyclo[3.1.0]hex-6-yl)ethylaminocarbonyl]naphth-1-yloxymethyl)oxazolidine residue which is then stirred in 50 ml. of diethyl ether and filtered. Gaseous hydrogen chloride is passed over the surface of the filtrate with rapid stirring until no further precipitate is formed. The precipitate is filtered off, washed with diethyl ether and then recrystallized from a mixture of propanol and diethyl ether affording 3-isopropyl-5-(4-[2-(endobicyclo[3.1.0]hex-6-yl)ethylaminocarbonyl]naphth-1-yloxymethyl)oxazolidine hydrochloride.

Similarly by following the same procedure, the products of Example 1 are respectively converted to the corresponding compounds bearing the substituent Ib and their hydrochloride salts.

Obviously many modifications and variations of the invention, described herein above and below in the claims, can be made without departing from the essence and scope thereof.

What is claimed is:

1. A compound of the formula

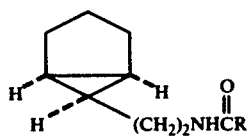

wherein R is

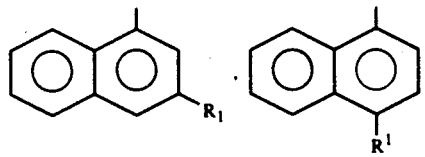

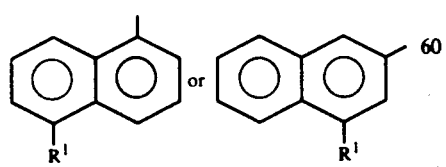

wherein $R^1$ is the radical $-OCH_2CH(OH)CH_2NHR^2$ wherein $R^2$ is $C_1$ to $C_4$ linear or branched alkyl, and the pharmaceutically acceptable salt thereof.

2. The compound of claim 1 wherein when said compound is a pharmaceutically acceptable salt, said salt selected from the group hydrochloride and maleate salt.

3. The compound of claim 1 where $R^2$ is isopropyl.

4. The compound of claim 3 wherein R is

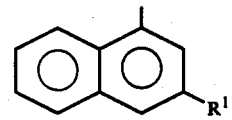

5. The compound of claim 3 wherein R is

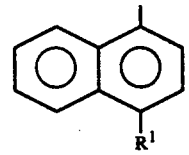

6. The compound of claim 3 wherein R is

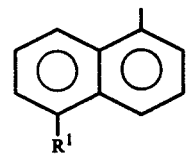

7. The compound of claim 3 wherein R is

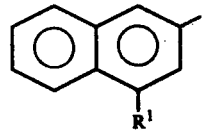

8. The compound of claim 1 where $R^2$ is t-butyl.
9. The compound of claim 8 wherein R is

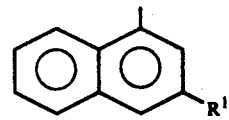

10. The compound of claim 8 wherein R is

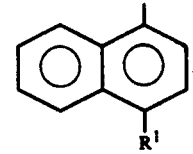

11. The compound of claim 8 wherein R is

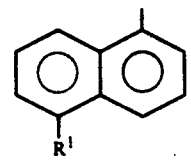

12. The compound of claim 8 wherein R is

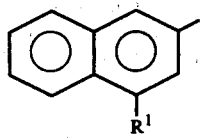

13. A pharmaceutical composition for treating cardiovascular disorders in mammals by blocking the beta-adrenergic receptor sites, consisting essentially of a pharmaceutically acceptable carrier and an amount effective to block said beta-adrenergic receptor sites of an agent selected from the group of compounds of claim 1.

14. A pharmaceutical composition for treating hypertension disorders in mammals consisting essentially of a pharmaceutically acceptable carrier and an amount effective to treat hypertension of an agent selected from the group of compounds of claim 1.

* * * * *